US011992634B2

(12) United States Patent
Haslam et al.

(10) Patent No.: US 11,992,634 B2
(45) Date of Patent: May 28, 2024

(54) ARTERIAL ACCESS NEEDLE WITH PROXIMAL PORT

(71) Applicant: Merit Medical Systems, Inc., South Jordan, UT (US)

(72) Inventors: Michael Dean Haslam, Sandy, UT (US); Richard P. Jenkins, Bluffdale, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 138 days.

(21) Appl. No.: 17/195,043

(22) Filed: Mar. 8, 2021

(65) Prior Publication Data

US 2021/0283377 A1 Sep. 16, 2021

Related U.S. Application Data

(60) Provisional application No. 62/987,672, filed on Mar. 10, 2020.

(51) Int. Cl.

*A61M 25/06* (2006.01)
*A61M 25/00* (2006.01)
*A61M 25/09* (2006.01)
*A61M 39/02* (2006.01)

(52) U.S. Cl.

CPC .... *A61M 25/0612* (2013.01); *A61M 25/0097* (2013.01); *A61M 25/065* (2013.01); *A61M 25/0693* (2013.01); *A61M 25/09* (2013.01); *A61M 2025/0098* (2013.01); *A61M 25/0637* (2013.01); *A61M 25/09025* (2013.01);

(Continued)

(58) Field of Classification Search

CPC ...... A61M 25/0693; A61M 2039/0244; A61M 25/0097; A61M 2025/0098; A61M 25/09; A61M 25/09041; A61M 2025/0687; A61M 2025/09083; A61M 5/3291; A61M 5/329; A61M 25/0612; A61M 25/065; A61M 25/0637; A61M 25/09025; A61M 2205/7536; A61B 5/1422

See application file for complete search history.

(56) References Cited

U.S. PATENT DOCUMENTS 5,246,426 A * 9/1993 Lewis ............... A61M 25/0693 604/168.01
5,366,441 A * 11/1994 Crawford .......... A61M 25/0606 604/510

(Continued)

FOREIGN PATENT DOCUMENTS

EP 0139091 5/1985

OTHER PUBLICATIONS

International Search Report and Written Opinion dated Jun. 30, 2021 for PCT/US2021/021365.

*Primary Examiner* — William R Carpenter
*Assistant Examiner* — Robert F Allen
(74) *Attorney, Agent, or Firm* — Dorsey & Whitney LLP

(57) ABSTRACT

Devices used to provide access the vasculature are disclosed. The devices may be configured to provide access to a blood vessel, such as an artery. The devices may include a catheter assembly disposed over a needle assembly. The devices may also include a barrel assembly coupled to the needle assembly. A guidewire may be displaceable by barrel assembly within a needle. The needle may include a proximal and distal port.

18 Claims, 13 Drawing Sheets

121 Blood Flow 155 190' 130 129 133 100 165 166 Blood Flow Blood Flow Blood Flow 176 151 191' 177 175 145 153 164

356 365 392 364 366" 300 366'

(52) U.S. Cl.
CPC ................. *A61M 25/09041* (2013.01); *A61M 2039/0244* (2013.01); *A61M 2205/7536* (2013.01)

(56) References Cited

U.S. PATENT DOCUMENTS 5,427,118 A * 6/1995 Nita ................ A61B 17/22012 600/585
5,599,296 A * 2/1997 Spears ..................... C01B 5/00 604/24
6,361,524 B1 3/2002 Odell et al.
6,743,216 B2 6/2004 Odell et al.
7,025,746 B2 4/2006 Tal
7,331,942 B2 2/2008 Alheidt et al.
7,682,342 B2 3/2010 Odell et al.
7,722,567 B2 5/2010 Tal
8,672,888 B2 3/2014 Tal
8,740,854 B2 6/2014 Schiller et al.
8,740,856 B2 6/2014 Quinn et al.
9,592,346 B2 3/2017 Quinn et al.
10,010,343 B2 7/2018 Bierman et al.
10,136,916 B2 11/2018 Bierman et al.
10,183,118 B2 1/2019 Quinn et al.
2004/0127859 A1 7/2004 Ward
2009/0187147 A1* 7/2009 Kurth ................ A61M 25/0606 604/161
2009/0221961 A1 9/2009 Tal et al.
2010/0069880 A1* 3/2010 Grayzel ........... A61M 25/0662 604/509
2011/0282285 A1 11/2011 Blanchard et al.
2015/0119847 A1* 4/2015 Wilson .................. A61M 25/09 604/529
2016/0331938 A1 11/2016 Blanchard et al.
2017/0043060 A1* 2/2017 Wang ...................... A61L 29/02
2017/0348511 A1 12/2017 Burkholz et al.
2021/0290913 A1* 9/2021 Horst ................... A61M 25/09

* cited by examiner 164
166
170
100
196
Blood Flow
183
175
195
176
175

ARTERIAL ACCESS NEEDLE WITH PROXIMAL PORT

RELATED APPLICATIONS

The present application claims priority to U.S. Provisional Application No. 62/987,672, filed on Mar. 10, 2020 and titled, "Arterial Access Needle with Proximal Port," which is hereby incorporated by reference in its entirety.

TECHNICAL FIELD

The present disclosure relates generally to medical devices, including devices used to access the cardiovascular system. In some embodiments, the present disclosure relates to vascular access devices comprising an extendable guidewire.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1A:
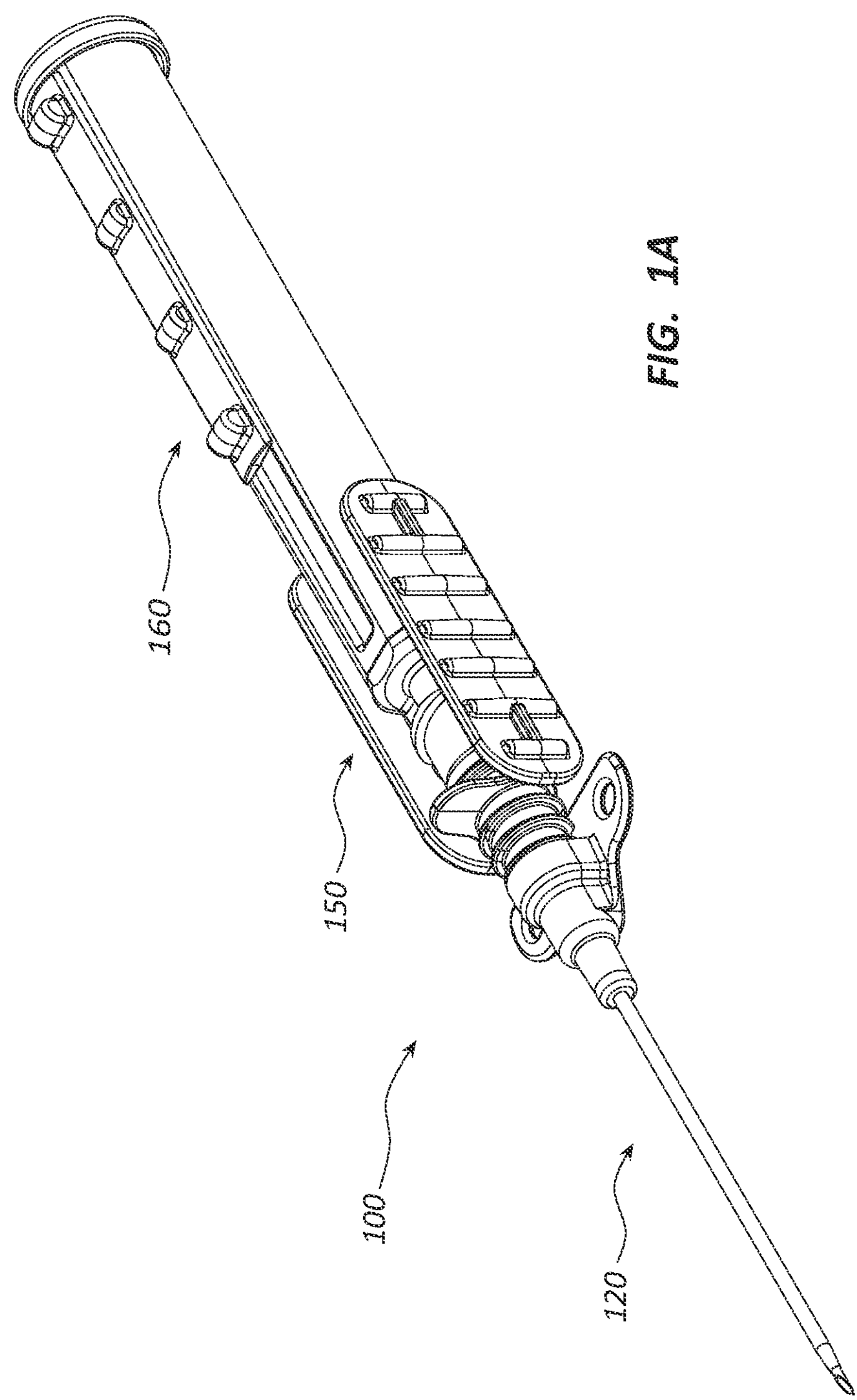
FIG. 1A is a perspective view of a vascular access device.

In some embodiments within the scope of this disclosure, a vascular access device may include a needle assembly, a catheter assembly, and a barrel assembly. The needle assembly may include a needle, and the catheter assembly may include an elongate catheter body coaxially disposed over a portion of the needle such that the catheter body may be inserted into a blood vessel over the needle of the needle assembly. The barrel assembly may include a guidewire slidably disposed within a lumen of the needle. The guidewire may be configured to facilitate insertion of the catheter assembly into the blood vessel.

Further, in some embodiments, the needle may comprise a distally located port and a proximally located port configured to divert blood flow from a needle lumen into an elongate annular space between the needle and the catheter body and then back into the needle lumen. The elongate annular space may be configured to allow observation of the flashback blood by a practitioner, for example, to confirm puncture of the blood vessel by the needle. The guidewire may include a distal portion that is positionable within the lumen such that it is configured to substantially occlude the needle lumen between the distally located port and the proximally located port when the distal portion is disposed between the distally located port and the proximally located port. Additionally, in some embodiments, the barrel assembly may include a flashback channel configured to allow the practitioner to further observe flashback blood.

Vascular access devices may be used to provide access to the vasculature to perform certain medical procedures. For example, a vascular access device may be used to withdraw blood samples, monitor pressure within the blood vessel, infuse fluids or medicaments into the blood vessel, introduce elongate medical devices or instruments into the blood vessel, or to provide access for other medical procedures. In some procedures within the scope of this disclosure, the vascular device may be inserted into the blood vessel by puncturing the blood vessel with the needle, visually observing flashback blood in the elongate annular space and/or the flashback channel, inserting the guidewire into the blood vessel, and inserting the catheter body into the blood vessel over the needle and/or guidewire.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluidic, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device refers to the end of the device furthest from the practitioner during standard use. The proximal end refers to the opposite end, or the end nearest the practitioner during use. As specifically applied to a needle assembly of a vascular access device, the proximal end of the needle assembly refers to the end nearest a hub and the distal end refers to the opposite end, the end nearest the sharp end of the needle. These terms do not change meaning if a practitioner temporarily changes the orientation or hand position on an assembly. Thus, as used herein, the term "proximal end" always refers to the hub end of the needle assembly (even if the distal end is temporarily closer to the practitioner).

"Fluid" is used in its broadest sense, to refer to any fluid, including both liquids and gases as well as solutions, compounds, suspensions, blood, etc., which generally behave as fluids.

FIGS. 1A-11 illustrate different views of vascular access devices and related components. In certain views the device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure may be relevant and applicable to disclosure provided in connection with any other figure or embodiment.

Figure 1B:
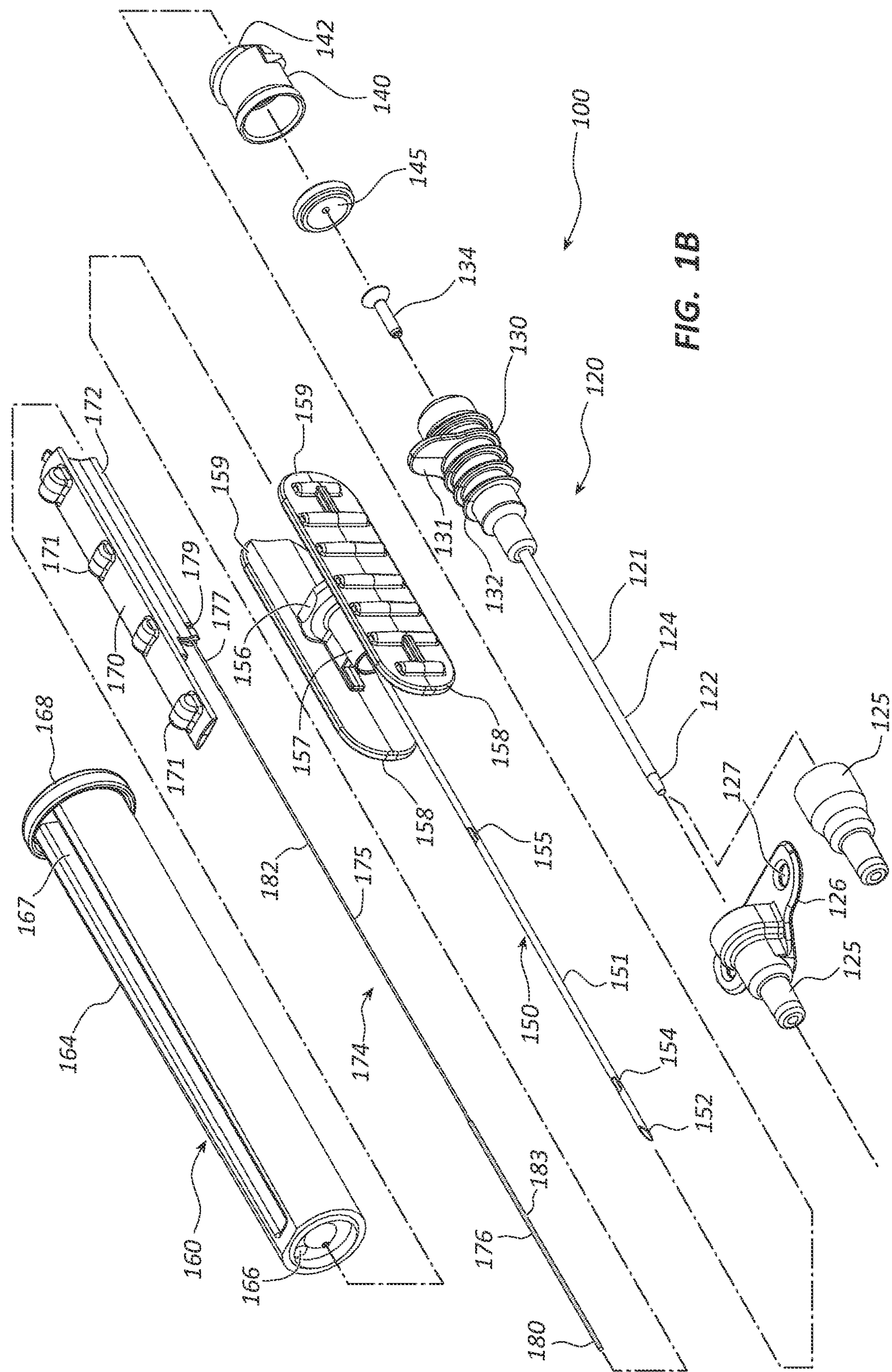
FIG. 1B is a perspective exploded view of the vascular access device of FIG. 1A.

FIGS. 1A-1B depict an embodiment of a vascular access device 100 where FIG. 1A is a perspective view and FIG. 1B is an exploded perspective view thereof. In the illustrated embodiment, the vascular access device 100 is partially comprised of a catheter assembly 120, a needle assembly 150, and a barrel assembly 160.

As depicted in the embodiment of FIGS. 1B-2B, the catheter assembly 120 may comprise a catheter body 121 and a catheter hub 129. The catheter body 121 may further include an elongate tube 124 having a lumen 123 extending a length of the tube 124. In some embodiments, an outer diameter of the tube 124 may range from about 14 gauge to about 24 gauge and a length of the tube 124 may range from about 0.50 inch to about 2.50 inch. In other embodiments within the scope of this disclosure, the length of the tube 124 may be longer or shorter, including lengths up to or greater than 12 inches. The tube 124 may comprise a biocompatible polymeric material, such that the tube 124 can be indwelling within a patient's blood vessel for a time period ranging from hours to several days while minimizing damage to the blood vessel. In other embodiments, the tube 124 may be formed from a material that facilitates blood pressure waveforms to be transmitted through the tube 124 without significant dampening of the waveform. For example, the tube 124 may be formed from polyurethane, fluorinated ethylene propylene (FEP), polyethylene, silicone, nylon, polyetheretherketone, etc.

In some embodiments, a radiopaque filler material may be incorporated into the wall of the tube 124 to increase the radiopacity level of the tube 124, such that the tube 124 is visible within a patient's body using X-ray or fluoroscopy. The radiopaque material may be evenly dispersed throughout the wall. In other embodiments, the radiopaque material may be contained in a concentrated longitudinal stripe. In another embodiment, the radiopaque material may be contained in a plurality of longitudinal stripes disposed in the wall of the tube 124. The radiopaque material may comprise medical-grade materials capable of absorbing X-ray radiation. For example, the radiopaque material may be barium sulfate, bismuth trioxide, bismuth subcarbonate, bismuth oxychloride, tungsten, etc. In certain embodiments, the tube 124 may be transparent or translucent to allow visualization of blood or other fluids within the lumen 123. In other embodiments, the tube 124 may be opaque.

The tube 124 may comprise a tapered tip 122 adjacent a distal end of the tube 124. The tapered tip 122 may facilitate insertion of the tube 124 into tissue. The tapered tip 122 may be formed using any suitable manufacturing method, such as heating of a die with radiofrequency energy, molding, stretching and skiving, extrusion, etc. In some embodiments, the lumen 123 adjacent the tapered tip 122 may form a seal around the needle (151 if FIB. 1B) when the needle (151 of FIG. 1B) is disposed within the lumen 123. A lubricant may be dispersed over an outer surface of the tube 124 to facilitate insertion of the tube 124 into tissue. The lubricant may be any suitable material, such as silicone, hydrogel, etc. In some embodiments, the tube 124 may be coated with other materials such as an antimicrobial agent to reduce a risk of a catheter-related blood stream infection, an anti-throbogenic agent to reduce a risk of a thrombus forming around the tube 124 causing occlusion of the blood vessel, etc.

With continued reference to FIGS. 1B-2B, in the illustrated embodiment, the proximal end of the tube 124 is coupled to the catheter hub 129. The catheter hub 129 may include a distal hub 130 coupled to a proximal hub 140. In other embodiments, the catheter hub may be formed as a single component. The distal hub 130 may include a bore 133 in fluid communication with the lumen 123 of the tube 124. A swage adapter 134 may be used to couple the proximal end of the tube 124 to the distal hub 130. In other embodiments, the tube 124 can be coupled to the distal hub 130 using other suitable techniques, such as bonding, gluing, welding, over molding, etc. In some embodiments, the distal hub 130 may include at least one suture ring 132 configured to facilitate securement of the catheter hub 129 to the skin of the patient using a suture. The distal hub 130 may also optionally include a push tab 131 extending radially outward. The push tab 131 may facilitate advancement of the catheter assembly 120 over the needle 151.

In some embodiments a strain relief member 125 may be disposed over a distal end of the distal hub 130 and a proximal portion of the tube 124 where the tube 124 enters the bore 133 of the distal hub 130. The strain relief member 125 may be configured to prevent or reduce kinking of the tube 124 at the junction between the tube 124 and the distal hub 130. Kinking of the tube 124 may disrupt fluid within the lumen, prevent withdrawal or infusion of fluids or medicaments through the tube 124, and/or interfere with transmission of blood pressure waveforms through the tube 124. The strain relief member 125 may be formed from a compliant material, such as thermoplastic elastomer, silicone, rubber, neoprene, etc., using any suitable manufacturing technique, such as injection molding, compression molding, casting, etc. The strain relief member 125 may be coupled to the distal hub 130 using any suitable technique, such as friction fit, solvent bonding, gluing, welding, over molding, etc.

In some embodiments, the strain relief member 125 may include a wing member 126 with two laterally extending wings to provide stabilization of the catheter assembly 120 on the skin of the patient. The wing member 126 may be a separate component or an integrated component with the strain relief member 125. The wing member 126 may be formed from the same material as the strain relief member 125 or a dissimilar material. For example, the wing member 126 may be formed from a material that is less compliant than the strain relief member 125, such that the wing member 126 provides improved stabilization of the catheter assembly 120. The wing member 126 may be formed from any suitable polymeric material, such as polypropylene, polyethylene, polycarbonate, thermoplastic elastomer, etc. The wing member 126 may include a suture hole 127. A suture may pass through the suture hole 127 and the patient's skin to stabilize and secure the catheter assembly 120 to the patient.

Figure 2A:
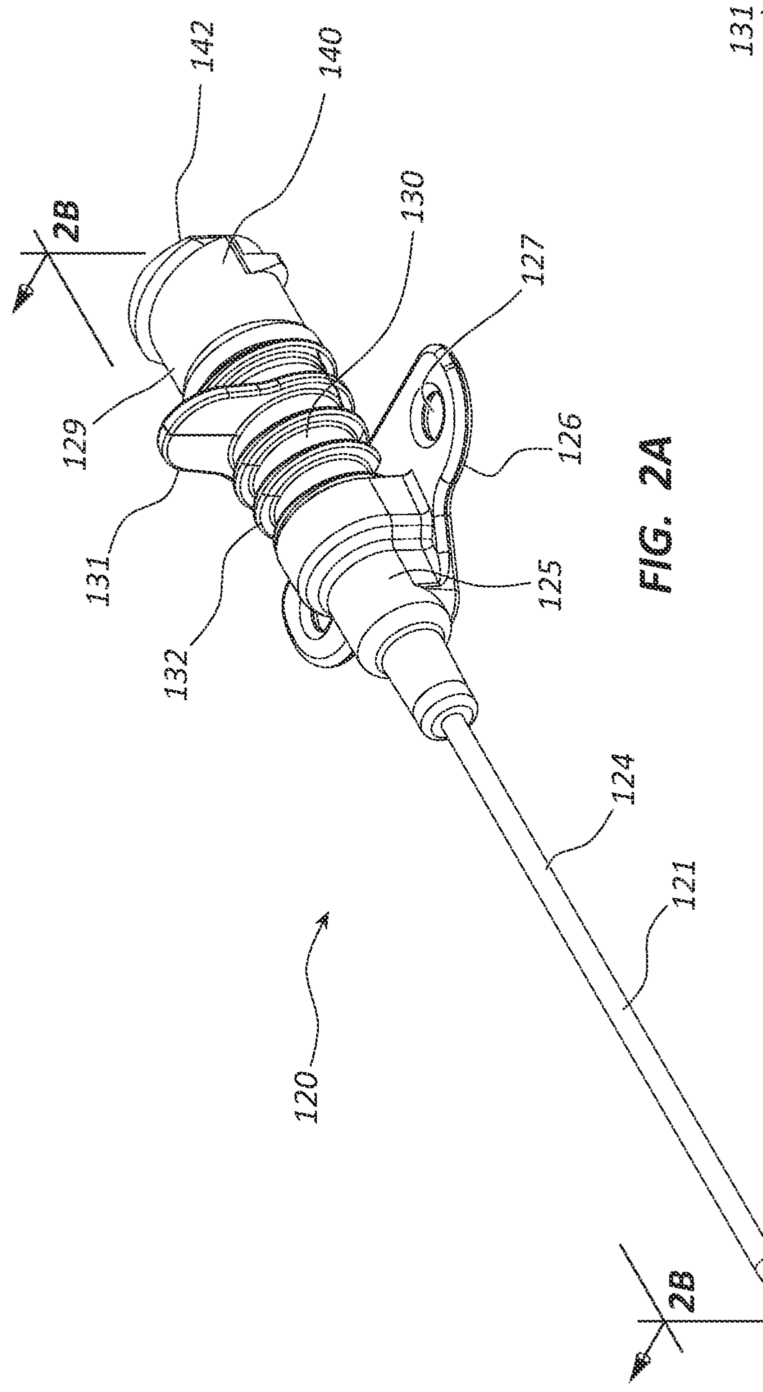
FIG. 2A is a perspective view of a catheter assembly of the vascular access device of FIG. 1A.
Figure 2B:
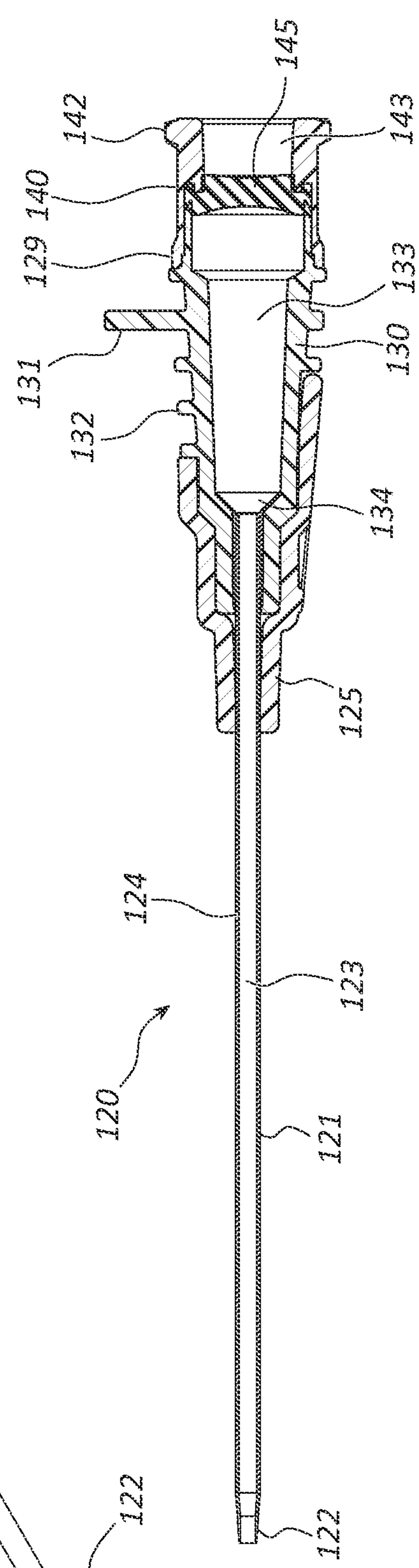
FIG. 2B is a longitudinal cross-sectional view of the catheter assembly of FIG. 2A.

In the illustrated embodiment of FIGS. 2A-2B, the distal hub 130 is coupled to the proximal hub 140. The distal hub 130 may be coupled to the proximal hub 140 to form a fluid tight seal using any suitable technique, such as friction fit, snap fit, bonding, gluing, welding, over molding, etc. The proximal hub 140 may comprise a bore 143 that is in fluid communication with the bore 133 of the distal hub 130 and open at a proximal end of the proximal hub 140. The bore 143 may be configured to sealingly receive a medical fitting having a protrusion (i.e., male luer fitting). External threads 142 may be disposed around an outer circumference of the proximal hub 140. The external threads 142 may be configured to engage with internal threads of a medical fitting to couple the medical fitting to the proximal hub 140.

In some embodiments, a valve member 145 may be disposed within the catheter hub 129. The valve member 145 may divide the bore 133 from the bore 143 and be configured to contain blood or other fluids within the bore 133. In other words, the valve member 145 may inhibit blood or other fluids from flowing out of the bore 133, into the bore 143, and out of the bore 143 to a location outside the vascular access device (100 of FIG. 1A). The valve member 145 of the embodiment illustrated in FIG. 2B is formed in the shape of a disc valve. In other embodiments, the valve member 145 may be formed in any suitable shape including shapes configured to contain blood or other fluids within the bore 133 and/or configured for being actuated or opened by a medical fitting. For example, the valve member 145 may be in the form of a duckbill valve, a flap valve, etc. A peripheral edge of the valve member 145 may be captured between the distal hub 130 and the proximal hub 140. In other embodiments, the valve member 145 may be coupled to the catheter hub 129 using any suitable technique. For example, the valve member 145 may be coupled to the catheter hub 129 by bonding, gluing, over molding, etc. The valve member 145 may be formed from any suitable compliant material, such as thermoplastic elastomer, silicone, neoprene, rubber, etc. The valve member 145 may be configured to form a fluid tight seal around the needle 151 when the needle 151 is disposed through the valve member 145. Furthermore, embodiments without a valve, or with valves disposed at different positions within the vascular access device 100 are likewise within the scope of this disclosure.

Figure 3A:
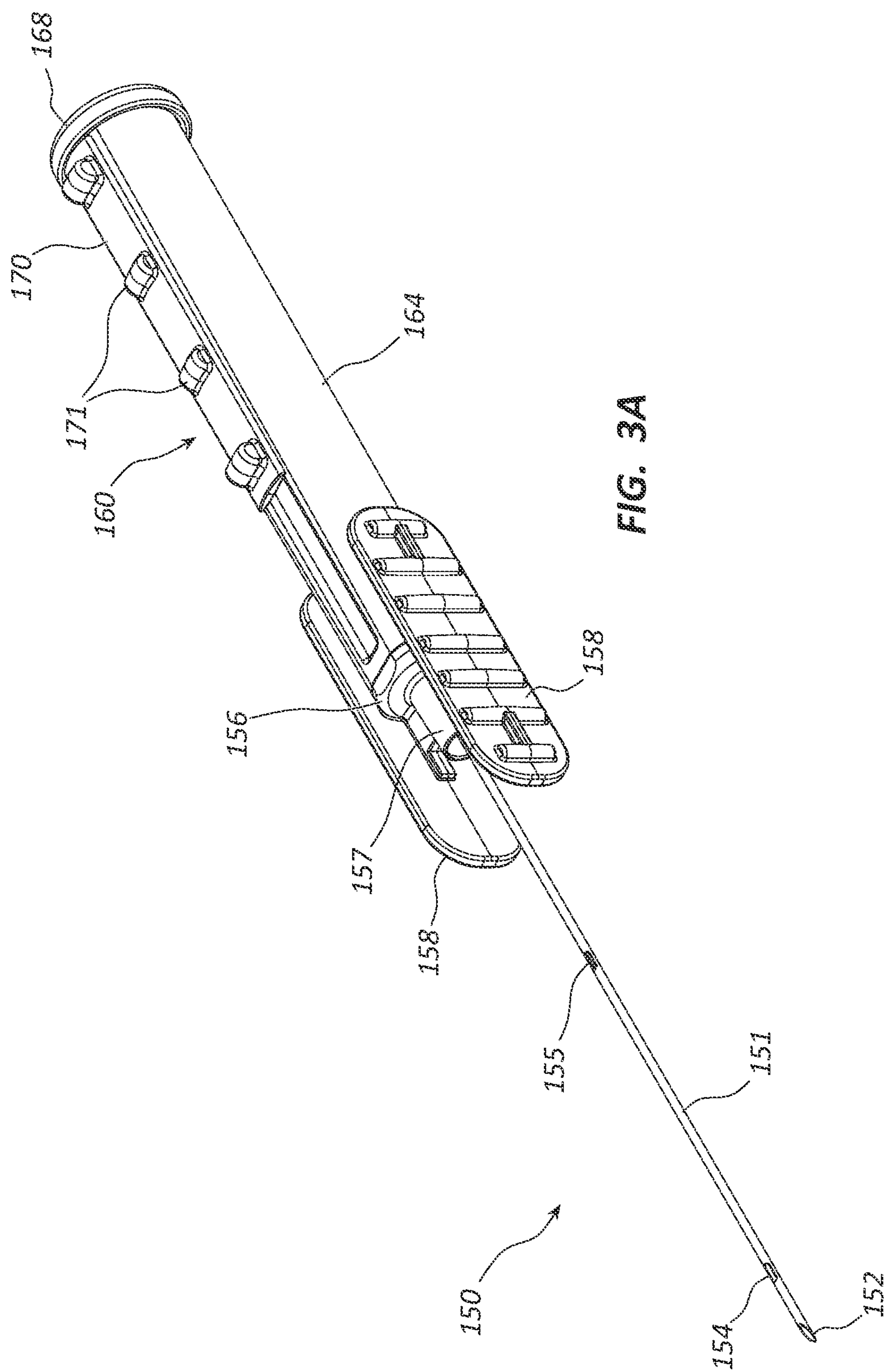
FIG. 3A is a perspective view of a needle assembly and a barrel assembly of the vascular access device of FIG. 1A.
Figures 3B, 3C:
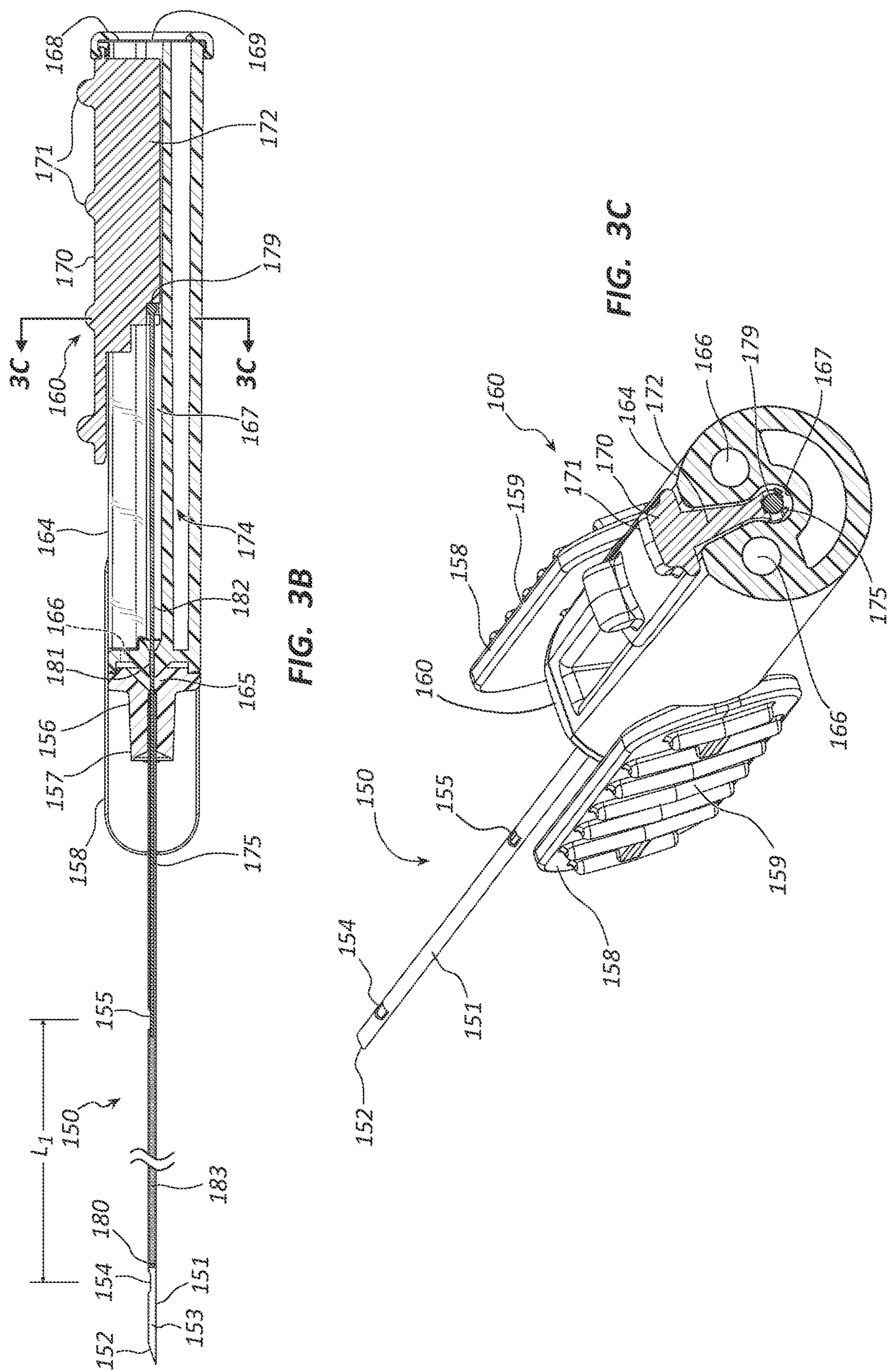
FIG. 3B is a longitudinal cross-sectional view of the needle assembly and barrel assembly of FIG. 3A.
FIG. 3C is a perspective cross-sectional view of the needle assembly and barrel assembly of FIG. 3A.

FIGS. 3A-3C illustrate the needle assembly 150 coupled to the barrel assembly 160 of the vascular access device 100. FIG. 3A is a perspective view of the needle assembly 150 and barrel assembly 160, FIG. 3B is a longitudinal cross-sectional view of the needle assembly 150 and barrel assembly 160, and FIG. 3C is a perspective cross-sectional view of the needle assembly 150 and barrel assembly 160 taken at plane 3C-3C of FIG. 3B. In the illustrated embodiment, the needle assembly 150 comprises a needle 151, a needle hub 156, and finger grips 158. The needle 151 is coupled to a nose 157 of the needle hub 156 and extends distally from the nose 157. The needle 151 may be coupled to the nose 157 using any suitable technique, such as bonding, gluing, welding, over molding, etc. In the illustrated embodiment, the needle 151 is shown to include a beveled sharp tip 152 disposed at a distal end. The needle tip 152 may be configured to puncture and/or cut tissue when the needle tip 152 is inserted into a patient.

The needle 151 may also include a distal port 154 disposed adjacent the needle tip 152 and a proximal port 155 disposed adjacent the nose 157. The ports 154, 155 may be notches in a wall of the needle 151 such that a needle lumen 153 is in communication with the ports 154, 155. The needle 151 may include a distance Li between the ports 154, 155. The needle 151 may be formed variety of materials, including rigid materials, such as stainless steel, nitinol, titanium, tungsten, etc. An exterior surface of the needle 151 may be coated with a lubricating material to reduce a needle penetration force and to facilitate advancement of the catheter assembly 120 over the needle 151. Coating materials within the scope of this disclosure include, but are not limited to, hydrophilic materials, hydrophobic materials, silicone, etc.

The needle hub 156 can be coupled to the proximal hub 140. The nose 157 may be sized, such as in length and/or diameter, to be received within the bore 143 of the proximal hub 140 without contacting the valve member 145. The finger grips 158 may include a pair of wings 159 disposed laterally on either side of the needle hub 156. The wings 159 may include grip-enhancing features, such as ridges, grooves, bumps, recesses, surface texturing, etc. A return chamber 165 may be disposed at a proximal end of the needle hub 156. As shown in the illustrated embodiment, the return chamber 165 may comprise a depression in the proximal end of the needle hub 156. The return chamber 165 may be in fluid communication with the needle lumen 153. The needle hub 156 may be formed of a variety of materials, including translucent or transparent polymeric materials, such as polycarbonate, acrylic, etc.

As depicted in FIGS. 3A-3C, the barrel assembly 160 may be coupled to the proximal end of the needle hub 156. The barrel assembly 160 may be coupled to the needle hub 156 variety of techniques, including techniques forming a fluid tight joint. For example, the joint may be formed by a friction fit, a snap fit, bonding, gluing, welding, over molding, etc. The barrel assembly 160 in the depicted embodiment includes an elongate barrel 164 and a guidewire assembly 174. In the illustrated embodiment, the barrel 164 is generally cylindrical and includes a flashback channel 166, a slider channel 167, and an end cap 168. Other shapes and features are likewise within the scope of this disclosure. The guidewire assembly 174 can include a slider 170 and a guidewire 175. The barrel 164 may be formed of a variety of materials, including polymeric materials, such as polycarbonate, acrylic, etc. In some embodiments, the barrel 164 may be transparent or translucent.

The flashback channel 166 may extend from a distal end to a proximal end of the barrel 164 or may extend along a portion of the length thereof. Various shapes and geometries of the flashback channel 166 are within the scope of this disclosure, including a flashback channel 166 with a circular cross-section. The flashback channel 166 may be in fluid communication with the return chamber 165 of the needle hub 156. In some embodiments, the barrel 164 may include a plurality of the flashback channels 166. For example, the number of the flashback channels 166 may be 2, 3, 4, 5, or more. The flashback channel 166 may extend linearly along the length of the barrel 164 and may have a uniform cross-section along its length. In other embodiments, the flashback channel 166 may be sized and configured such that the cross-sectional shape of the flashback channel 166 changes over a length of the barrel 164. For example, in embodiments where the cross-sectional shape of the flashback channel 166 becomes larger along the length of the flashback channel 166, the volume enclosed by the flashback channel 166 may be greater that a flashback channel 166 with a constant cross-sectional shape. Greater volume within the flashback channel 166 may correspond to an increase a flashback time in use. Furthermore, embodiments wherein the flashback channel 166 is curved or otherwise non-linear are within the scope of this disclosure. For example, the flashback channel 166 may be circuitous from the distal end to the proximal end of the barrel 164. The barrel 164 may be transparent or translucent such that blood within the flashback channel 166 may be visualized by the practitioner. Modifying the length, volume, cross section, and/or path of the flashback channel 166 may enable the flashback channel 166 to be configured to fill with visible blood at a desired rate. In other words, the flashback channel 166 may be tuned to fill in such a manner as to provide ease of use with respect to the amount of visible blood, the rate at which the blood becomes visible to a user, and so forth. For example, in some embodiments the cross section and/or other parameters of the flashback channel 166 may be configured such that the fill rate of the flashback channel 166 and/or the rate at which blood in the flashback channel 166 becomes visible to a user may be configured such that the rate of visualization or fill facilitates ease of use of the vascular access device 100.

An end cap 168 may cover the proximal end of the barrel 164 and the flashback channel 166. The end cap 168 may be configured to retain the slider 170 within the barrel 164. The end cap 168 may comprise a membrane 169 configured to allow air to vent from the flashback channel 166 as the flashback channel 166 fills with blood and to inhibit blood from leaking from the flashback channel 166 when filled.

A slider 170 may be slidingly coupled to the barrel 164. A downwardly extending protrusion 172 may be slidingly disposed within the slider channel 167 such that the slider 170 may be displaced longitudinally relative to the barrel 164. The protrusion 172 may be retained within the slider channel 167 to prevent the slider 170 from being displaced from the barrel 164. The slider 170 may include ribs 171 disposed on an upper surface. The ribs 171 may improve the gripability of the slider 170 by a practitioner's finger. In other embodiments, the slider 170 may include other grip-enhancing features, such as grooves, bumps, recesses, surface texturing, etc.

The guidewire 175 may be coupled to and extend distally from the protrusion 172. The guidewire 175 may slidingly pass through a passage 181 disposed at the distal end of the barrel 164. A diameter of the passage 181 may be sized to allow the guidewire 175 to be longitudinally displaced and to inhibit blood from passing from the return chamber 165 through the passage 181. The guidewire 175 may be disposed such that it is in axial alignment with a longitudinal axis of the needle 151. A portion of the guidewire 175 may be slidingly disposed within the needle lumen 153.

Figure 4:
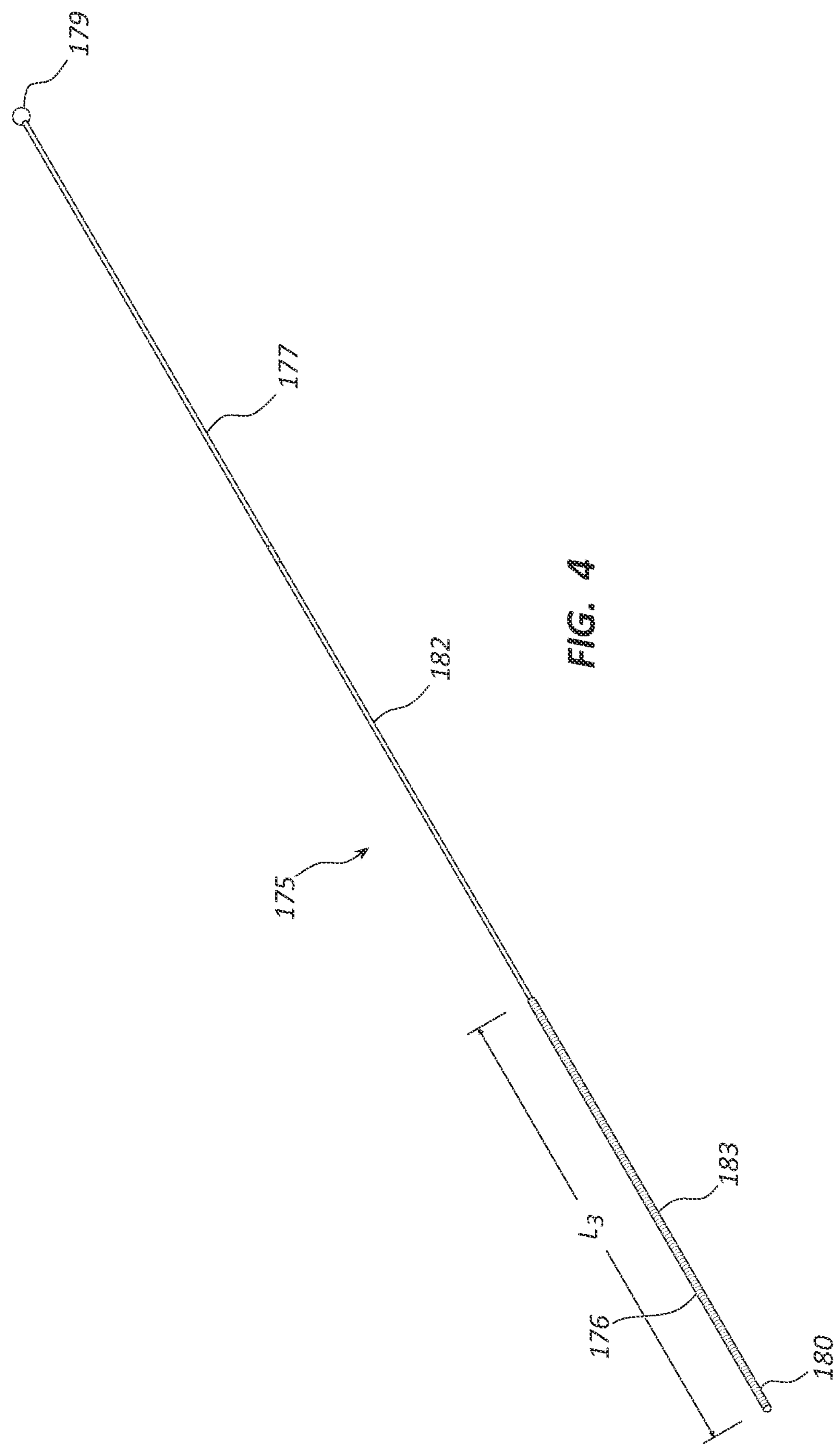
FIG. 4 is a perspective view of a guidewire of the vascular access device of FIG. 1A.

FIG. 4 is a perspective view of the guidewire 175 of the vascular access device 100. As shown in FIG. 4, the guidewire 175 may include an elongate mandrel 182 having a proximal portion 177 and a distal portion 176. The mandrel 182 may be formed from a variety of materials, including rigid materials, such as stainless steel, nitinol, titanium, tungsten, rigid polymers, etc. A spherical member 179 may be disposed at a proximal end of the mandrel 182. The spherical member 179 may be used to couple the mandrel 182 to the protrusion 172 of the slider 170. In other embodiments, including embodiments with no spherical member 179, the mandrel 182 may be coupled to the protrusion 172 using a variety of techniques, such as bonding, gluing, welding, over molding, etc. The proximal portion 177 may be rod shaped and have a diameter ranging from about 0.008 inch to about 0.018 inch, though larger and smaller diameters are likewise within the scope of this disclosure. The diameter of the proximal portion 177 may be smaller than the diameter of the needle lumen 153 such that blood may flow around the proximal portion 177 within the needle lumen 153. The distal portion 176 may be tapered toward a distal end 180 such that the distal portion 176 of the mandrel 182 is more flexible than the proximal portion 177.

In some embodiments, a coil 183 may be disposed around the distal portion 176 of the guidewire 175. The coil 183 can be configured to allow the distal portion to 176 flex without kinking the mandrel 182 when the guidewire 175 encounters an obstruction during advancement into the blood vessel. In some embodiments, the distal portion 176 is linear. In other embodiments, the distal portion 176 may form a J shape or other geometries when the distal portion 176 is unrestrained by the needle lumen 153. A diameter of the coil 183 may be larger than the diameter of the proximal portion 177 and slightly smaller than the diameter of the needle lumen 153 into which the coil 183 is disposed. In other words, the coil 183 may be configured such that it partially or substantially occludes the needle lumen 153, thus tending to inhibit blood from flowing around the coil 183 within the needle lumen 153. The coil 183 may be welded to the distal end 180 of the mandrel 182 such that the weld forms a hemispherical tip.

With reference to FIGS. 3A-4, the ports 154, 155 of the needle 151 may be configured to facilitate blood flow past the coil 183 toward the flashback channel 166. For example, the coil 183 may have a length L3 which is less than length Li such that the coil 183 may be disposed between the distal port 154 and proximal port 155 when the coil 183 is disposed within the needle lumen 153 in a ready state. While the coil 183 may partially or substantially occlude the needle lumen 153 between the ports 154, 155 (such that blood flow is inhibited within the needle lumen 153 between the ports 154, 155), the ports 154, 155 may be configured to provide an alternate flow path around the outside of the needle 151 in an annular space between the needle 151 and the lumen (123 of FIG. 2B) of the catheter body (121 of FIG. 2B).

Figure 5A:
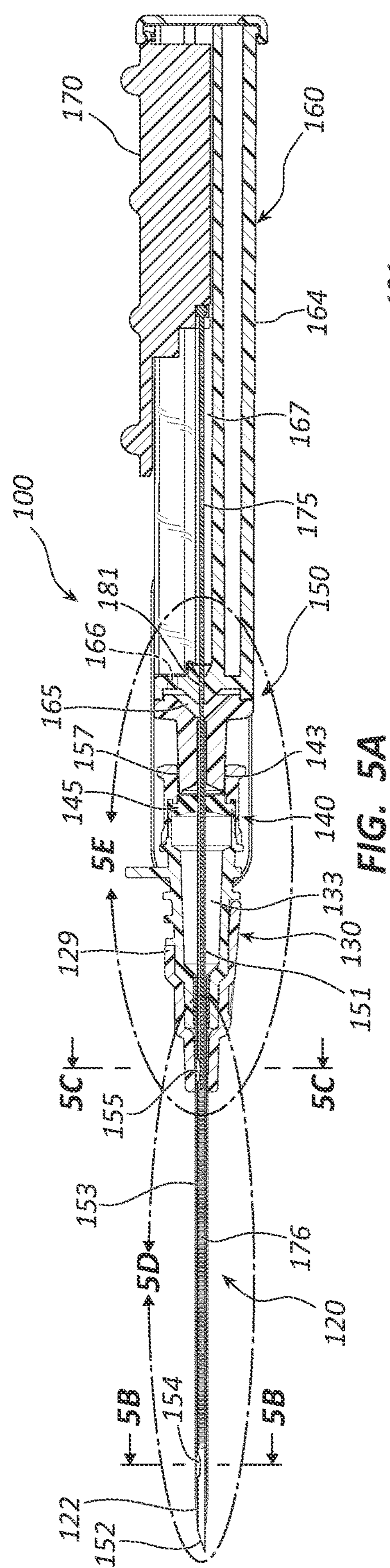
FIG. 5A is a longitudinal cross-sectional view of the vascular access device of FIG. 1A.
Figure 5C:
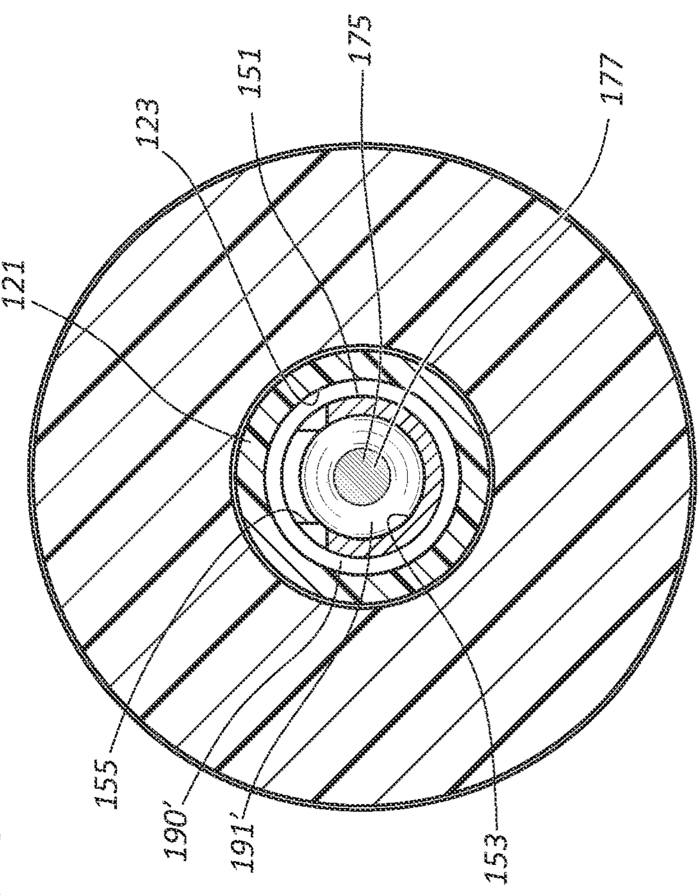
FIG. 5C is a transverse cross-sectional view of the vascular access device of FIG. 5A.
Figure 5B:
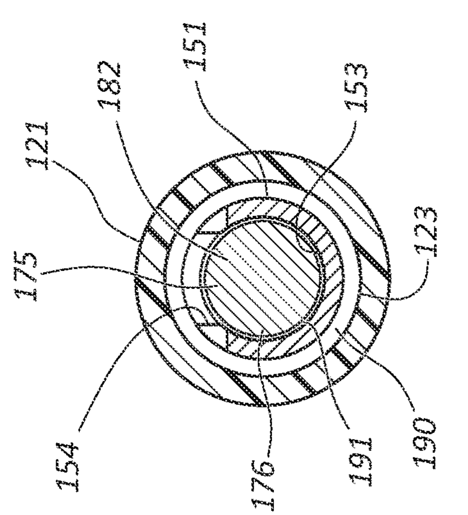
FIG. 5B is a transverse cross-sectional view of the vascular access device of FIG. 5A.
Figure 5D:
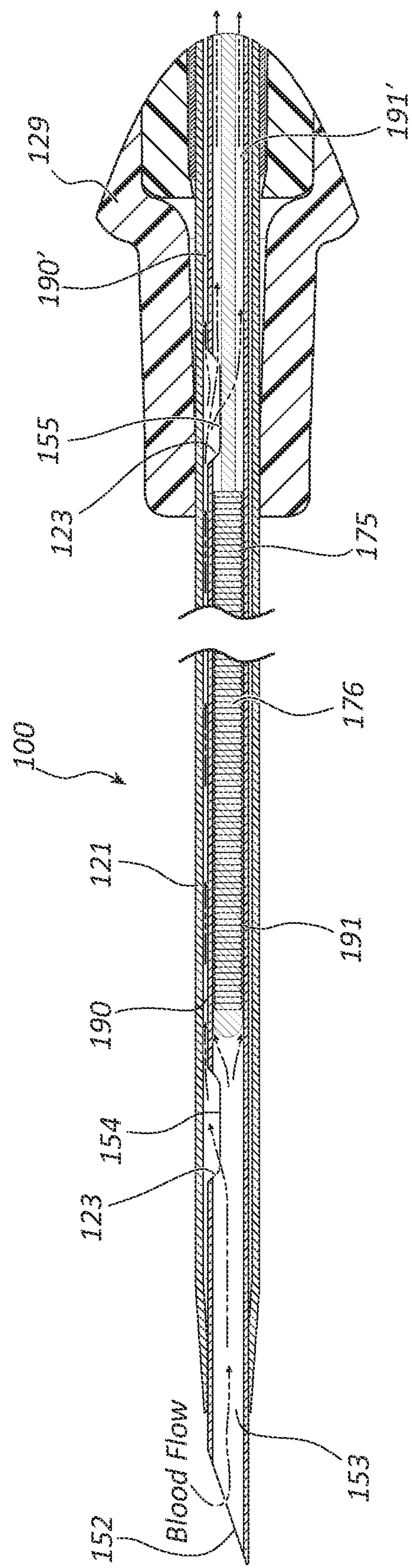
FIG. 5D is a detail view of a distal portion of the longitudinal cross-sectional view of FIG. 5A.
Figure 5E:
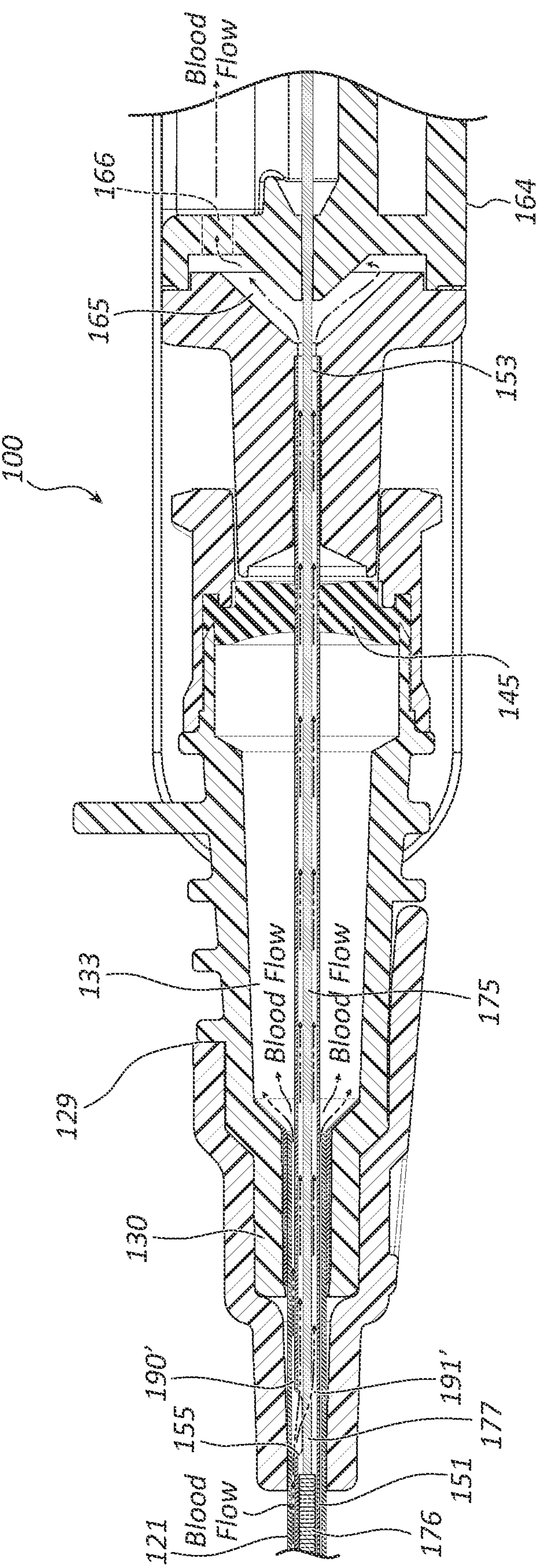
FIG. 5E is a detail view of a proximal portion of the longitudinal cross-sectional view of FIG. 5A.

FIGS. 5A-5E are various cross-sectional views of the vascular access device 100. FIG. 5A is a longitudinal cross-sectional view of the vascular access device 100. FIG. 5B is a transverse cross-sectional view from a distal perspective taken through plane 5B-5B of FIG. 5A. FIG. 5C is a transverse cross-sectional view from a distal perspective through plane 5C-5C of FIG. 5A. FIG. 5D is a detail view of a distal portion of the longitudinal cross-sectional view of FIG. 5A taken around section 5D of FIG. 5A. FIG. 5E is a detail view of a proximal portion of the longitudinal cross-sectional view of FIG. 5A taken around section 5E of FIG. 5A.

In the configuration of FIGS. 5A-5E, the vascular access device 100 is in a ready state. In the ready state, the catheter assembly 120 is co-axially disposed over the needle 151. The tapered tip 122 is disposed adjacent to and proximal to the needle tip 152 such that the tapered tip 122 may form a seal around the needle 151. The catheter hub 129 is removably coupled to the needle hub 156 such that the nose 157 is disposed within the bore 143 of the proximal hub 140 adjacent to the valve member 145. The needle 151 extends distally from the needle hub 156, through the valve member 145, through the bore 133 of the distal catheter hub 130, through the lumen 123, and extends distally beyond the tapered tip 122. The guidewire 175 is coupled to the slider 170 and extends distally through the slider channel 167, through the passage 181, through the return chamber 165, through the needle lumen 153, such that the distal portion 176 is disposed between the distal port 154 and the proximal port 155. The slider 170 is disposed adjacent the proximal end of the barrel 164 of the barrel assembly 160.

As shown in FIG. 5B, in the ready state, the distal portion 176 of the mandrel 182 is co-axially disposed within the needle lumen 153 proximal to the distal port 154. An annular space 191 is formed between an outer surface of the distal portion 176 and an inner surface of the needle 151. The annular space 191 may extend proximally from the distal end of the distal portion 176 to the proximal end of the distal portion 176. The needle 151 is co-axially disposed within the lumen 123 of the catheter body 121. An annular space 190 is formed between an outer surface of the needle 151 and an inner surface of the catheter body 121. The annular space 190 may extend proximally from the distal port 154 to the proximal port 155. A width of the annular space 190 may be larger than a width of the annular space 191. The annular space 190 may be in fluid communication with the needle lumen 153 through the distal port 154.

As shown in FIG. 5C, in the ready state, the proximal portion 177 of the guidewire 175 is co-axially disposed within the needle lumen 153. An annular space 191' is formed between an outer surface of the mandrel 182 and an inner surface of the needle 151. The annular space 191' may extend proximally from the proximal port 155 to the proximal end of the needle lumen 153. The needle 151 is co-axially disposed within the lumen 123 of the catheter body 121. An annular space 190' is formed between an outer surface of the needle 151 and an inner surface of the catheter body 121. The annular space 190' may extend proximally from the proximal port 155 to the proximal end of the catheter body 121. A width of the annular space 190' may be smaller than a width of the annular space 191'. As shown in the illustrated embodiment, the annular space 190' is in fluid communication with the annular space 191' through the distal port 154.

FIGS. 5D and 5E illustrate proximal and distal portions of the vascular access device 100 to show a flashback blood flow path from a distal end of the vascular access device 100 to a proximal end of the vascular access device 100. Visualization of flashback blood by a practitioner during insertion of the vascular access device 100 may be used as an indicator of puncture of a blood vessel. For example, flashback blood may be configured to flow through the needle 151 and/or catheter body 121 and into the flashback channel 166. The practitioner may visualize the flashback in the flashback channel 166 to confirm puncture of the blood vessel. The position of the guidewire 175 within the needle 151 may tend to occlude or slow blood flow through the needle lumen 153. As further detailed below, the ports 154, 155 may be configured to provide additional flow area to facilitate blood flashback into the flashback channel 166.

As compared to FIGS. 5A-5C, FIGS. 5D and 5E also include arrows to indicate a flow path of flashback blood through the vascular access device 100. In the depicted embodiment, flashback blood enters a distal opening of the needle lumen 153 when a blood vessel is punctured by the needle tip 152. The flashback blood flows through the needle lumen 153 until the flow is obstructed by the distal portion 176 of the mandrel 182 which is positioned proximal to the distal port 154. The flashback blood then flows primarily through the distal port 154 into the annular space 190. A smaller amount of flashback blood may flow into the annular space 191 due to the width of the annular space 191 being smaller than the width of the annular space 190. The flashback blood then flows proximally through the annular space 190 where it can be visualized by the practitioner until it reaches the proximal port 155. The flashback blood then flows primarily through the proximal port 155 into the annular space 191'. A smaller amount of flashback blood may flow through the annular space 190' toward the catheter hub 129 due to the width of the annular space 190' being smaller than the width of the annular space 191' and a flashback blood flow restriction formed by the valve member 145. The flashback blood then exits the proximal end of the needle lumen 153 and flows into the return chamber 165. The flashback blood then flows into the flashback channel 166 and can fill the flashback channel 166 from a proximal end to a distal end thereof. The flashback blood can be visualized again for an extended period of time as the flashback blood fills the flashback channel 166. The fill time of the flashback channel 166 allows the practitioner to further manipulate the tapered tip 122 within the blood vessel to achieve a position for insertion of the catheter body 121 into the blood vessel. The fill time may be dependent on blood pressure, volume of the flashback channel 166, and porosity of the vent membrane 169.

Figure 6A:
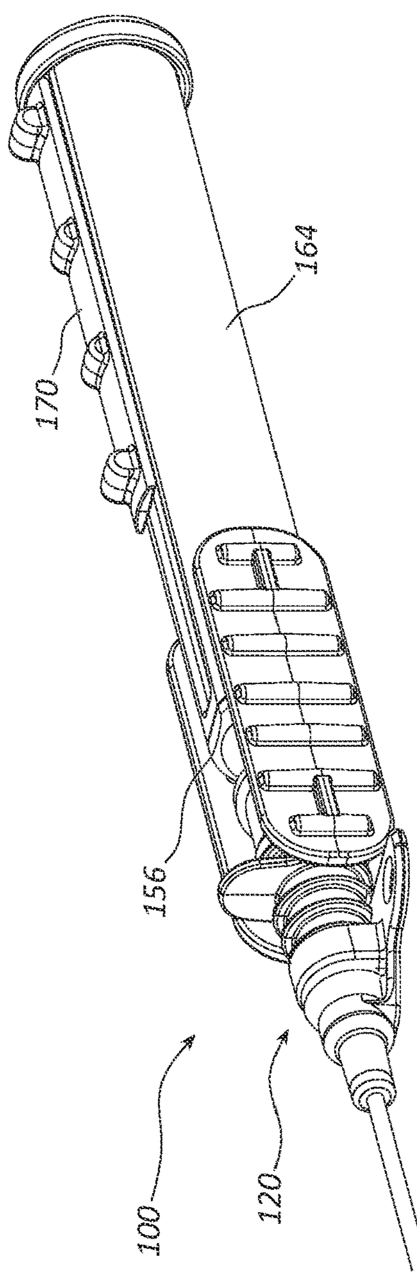
FIG. 6A is a perspective view of the vascular access device of FIG. 1A in a ready state.
Figure 6B:
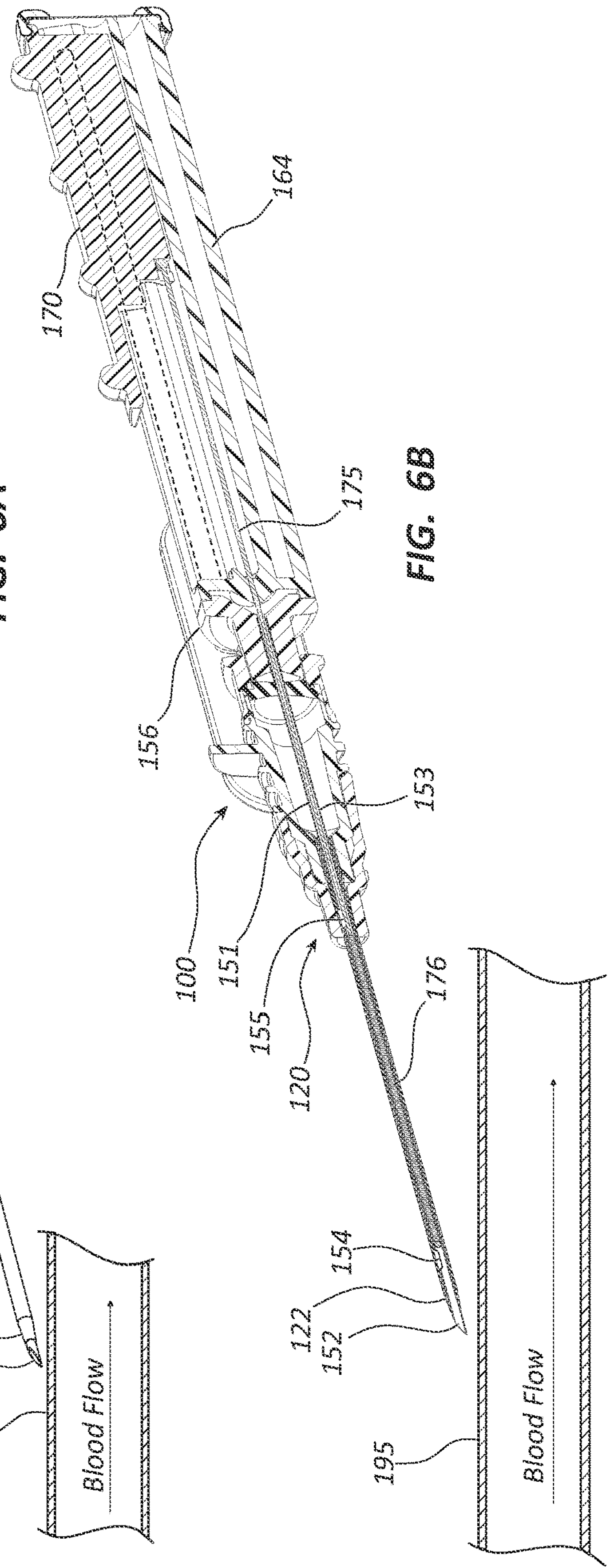
FIG. 6B is a perspective cross-sectional view of the vascular access device of FIG. 6A.

FIGS. 6A-9B illustrate the vascular access device 100 in use. FIGS. 6A and 6B depict the vascular access device 100 in the ready state prior to puncture of a blood vessel 195. The blood vessel 195 may be an artery or a vein, for example. As shown, the catheter assembly 120 is disposed over the needle 151 and coupled to the needle hub 156. The needle tip 152 extends distally beyond the tapered tip 122. The slider 170 is in a proximal position relative to the barrel 164. The distal portion 176 of the guidewire 175 is disposed within the needle lumen 153 and positioned between the distal port 154 and the proximal port 155. The distal portion 176 of the guidewire 175 may thus be positionable between the distal port 154 and the proximal port 155.

Figure 7A:
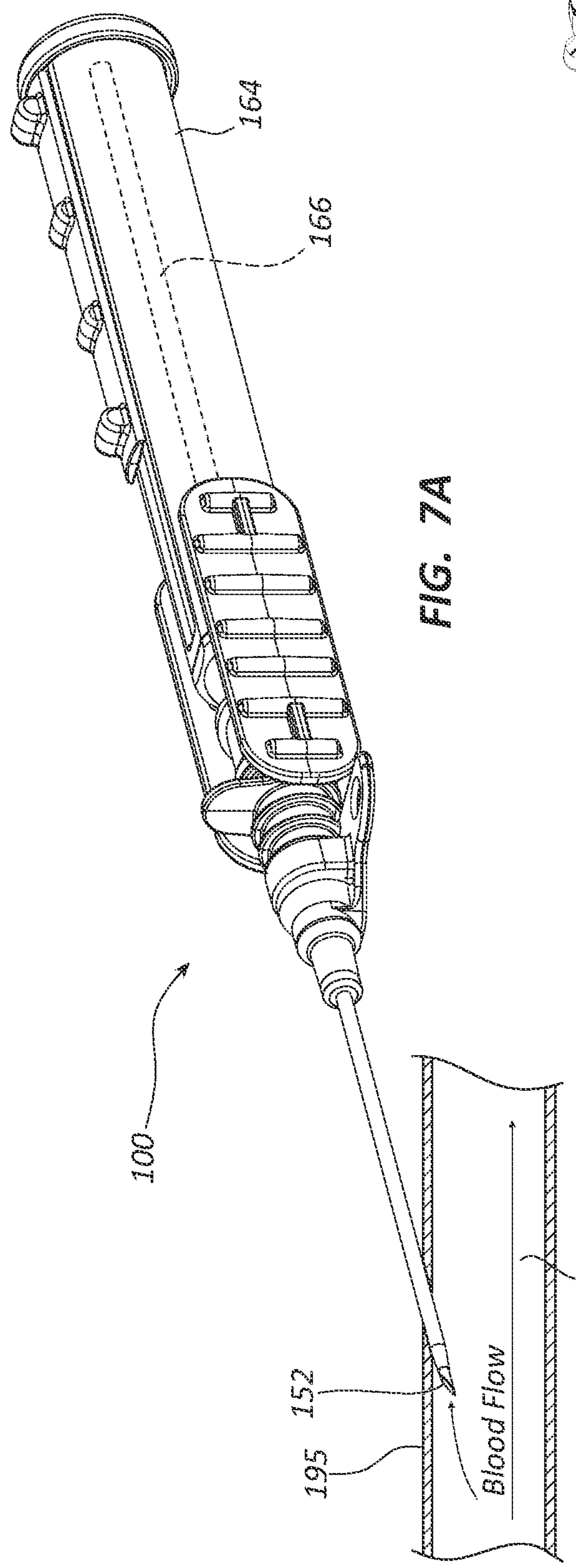
FIG. 7A is a perspective view of the vascular access device of FIG. 1A following insertion into a blood vessel.
Figure 7B:
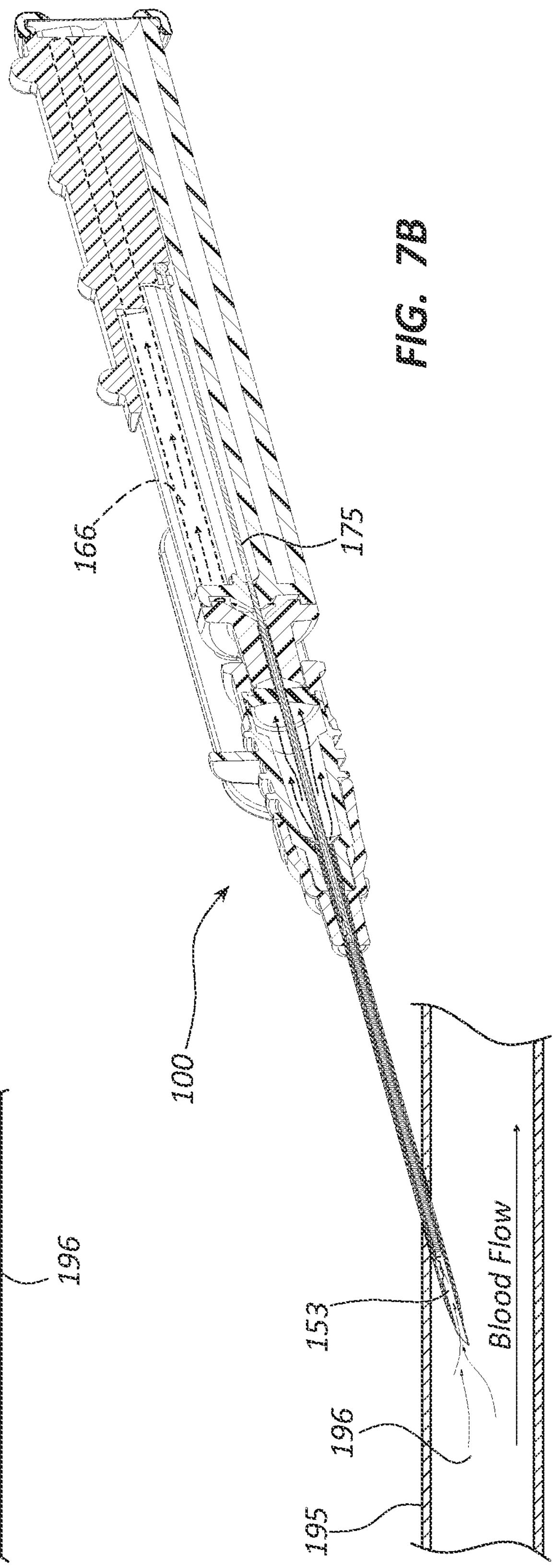
FIG. 7B is a perspective cross-sectional view of the vascular access device of FIG. 7A

FIGS. 7A and 7B depict the vascular access device 100 following puncture of the blood vessel 195 by the needle tip 152. Upon puncture of the blood vessel 195 and entrance of the needle tip 152 into a vessel lumen 196, flashback blood enters the needle lumen 153 at the needle tip 152. Thus, in some embodiments, inserting the needle tip 152 into a vessel lumen 196 may induce blood flow through the needle. The flashback blood then flows through the vascular access device 100 as previously described allowing the practitioner to visualize the flashback blood in the annular space 190 and in the flashback channel 166. (For example, as described above, blood may flow out of the distal port 154 and into the proximal port 155 when the distal portion of the guidewire 175 is disposed between these ports 154, 155.) The practitioner may manipulate the vascular access device 100 further as the flashback channel 166 fills to ensure that the needle tip 152 is adequately positioned in the vessel lumen 196 prior to advancement of the guidewire 175.

Figures 8A, 8B:
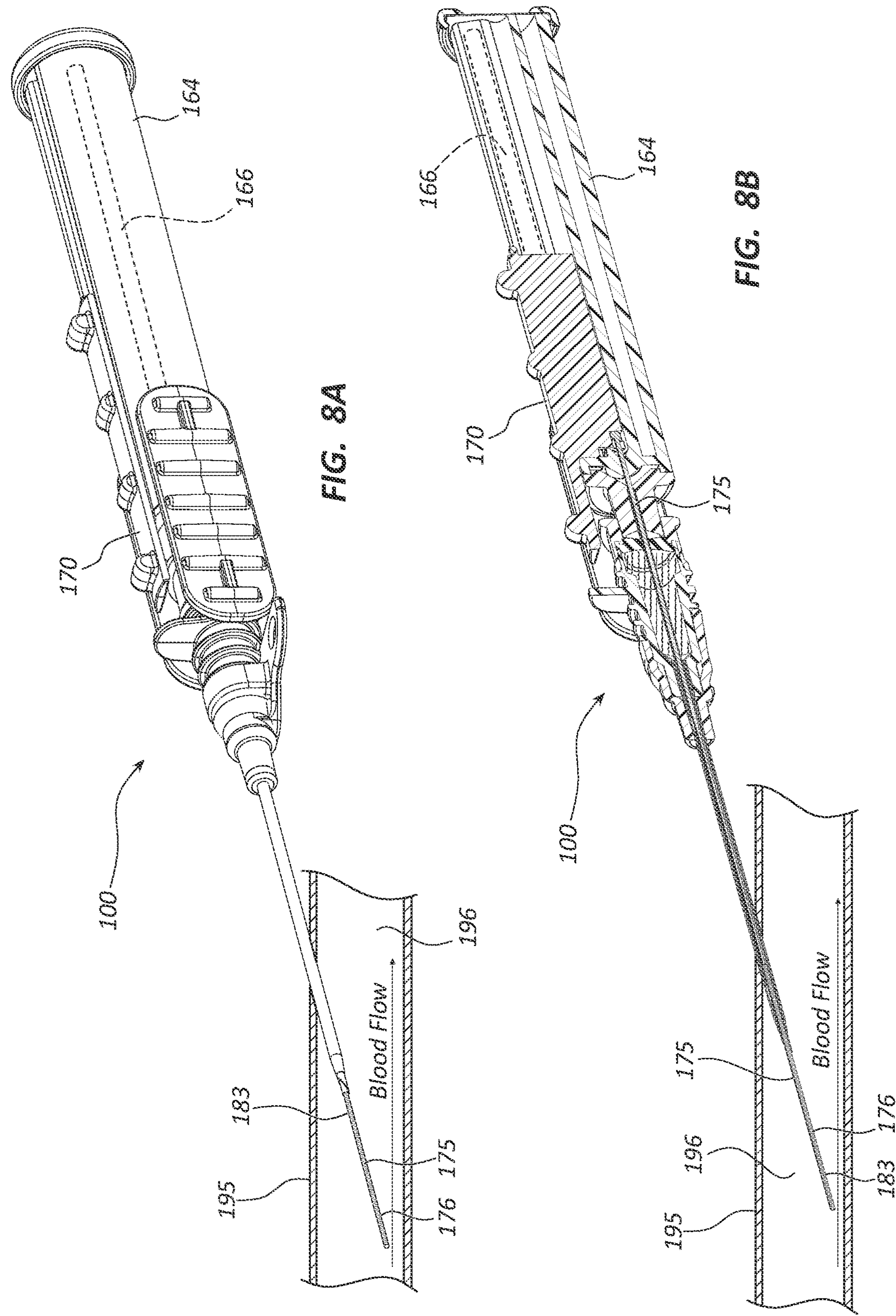
FIG. 8A is a perspective view of the vascular access device of FIG. 1A following advancement of the guidewire into the blood vessel.
FIG. 8B is a perspective cross-sectional view of the vascular access device of FIG. 8A.

FIGS. 8A and 8B depict the vascular access device 100 following distal advancement of the guidewire 175 where the distal portion 176 of the guidewire 175 is disposed within the vessel lumen 196. The slider 170 may be displaced from the proximal position to a distal position relative to the barrel 164 by a finger of the practitioner. Displacement of the slider 170 causes the guidewire 175 to be displaced distally. The guidewire 175 may be displaced until the distal portion 176 is disposed within the vessel lumen 196. The coil 183 may permit the distal portion 176 to flex if contact with an obstruction is encountered allowing the distal portion 176 to maneuver past the obstruction.

Figure 9B:
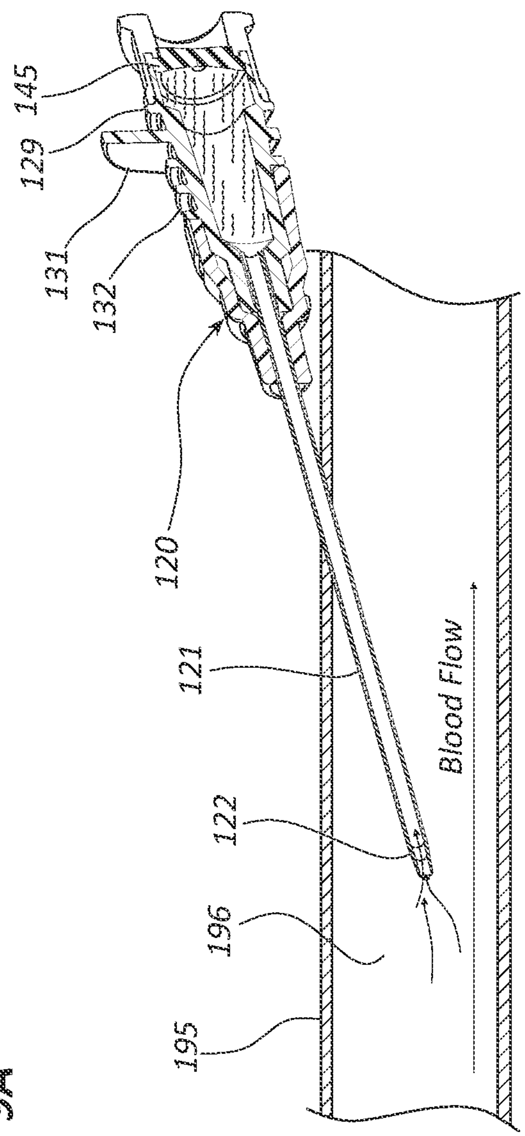
FIG. 9B is a perspective cross-sectional view of the catheter assembly of FIG. 9A.
Figure 9A:
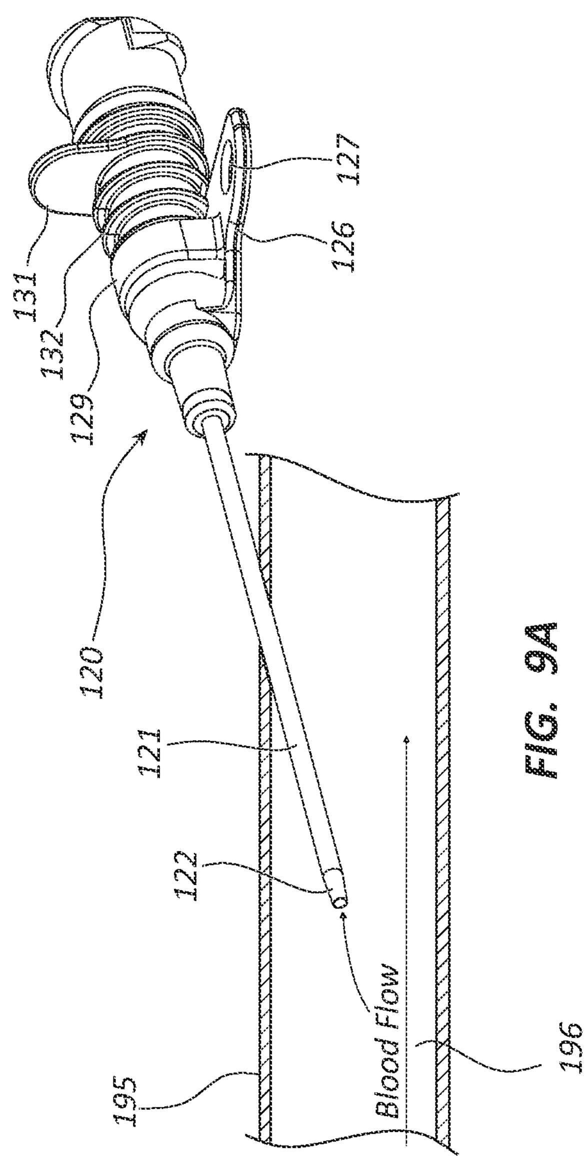
FIG. 9A is a perspective view of the catheter assembly of the vascular access device of FIG. 1A following advancement of the catheter assembly into the blood vessel.

FIGS. 9A and 9B depict the catheter assembly 120 following placement into the blood vessel 195 where the tapered tip 122 and a portion of the catheter body 121 are disposed within the lumen 196. The tapered tip 122 and the catheter body 121 may be inserted into the vessel lumen 196 when the practitioner grasps the catheter hub 129 and distally displaces the catheter assembly 120 over the needle (151 of FIG. 1B) and guidewire (175 of FIG. 1B). In other embodiments, the practitioner may distally displace the catheter assembly 120 by applying a digital pressure to the push tab 131. The guidewire 175 may guide the catheter body 121 through the vessel lumen 196. The valve member 145 may inhibit blood from flowing from the vessel lumen 196, through the catheter assembly 120, and exiting the catheter assembly 120.

Following placement of the catheter assembly 120, the catheter assembly 120 may be secured to the skin of the patient with tape or an adhesive dressing. In other embodiments, the catheter assembly 120 may be secured to the skin of the patient by operably coupling a suture with the suture rings 132 and the patient's skin. In another embodiment, the catheter assembly 120 may be secured to the skin of the patients by operably coupling the suture with the suture rings 132 through the suture holes 127 and the patient's skin.

The catheter assembly 120 may be used for a variety of medical procedures that include vascular access. For example, the catheter assembly 120 may be used to withdraw blood samples from a blood vessel, infuse fluids or medicaments into the blood vessel, continuously monitor pressure within the blood vessel, introduce medical devices or instruments into the blood vessel, etc.

Figure 10:
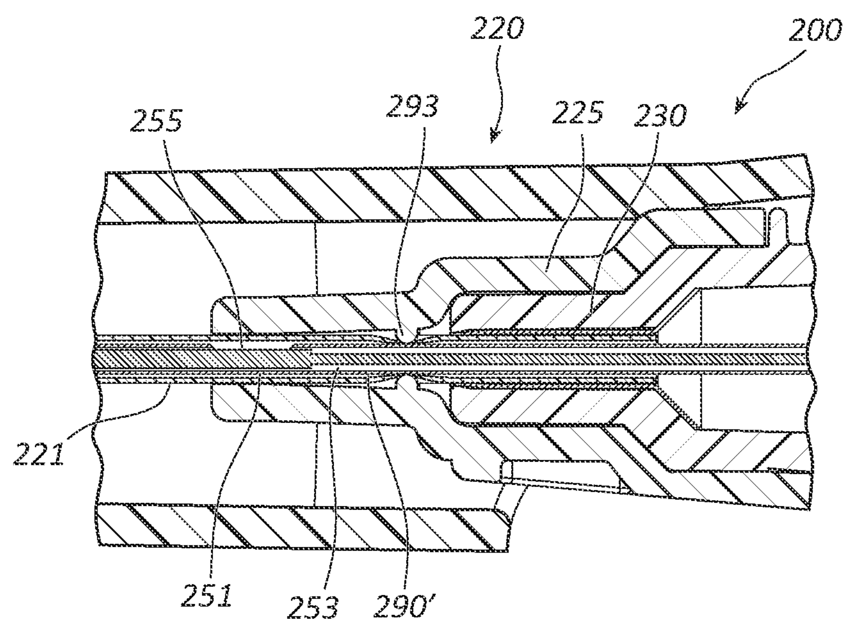
FIG. 10 is a cross-sectional view of a portion of another vascular access device.

FIG. 10 depicts an embodiment of a vascular access device 200 that resembles the vascular access device 100 described above in certain respects. Accordingly, like features are designated with like reference numerals, with the leading digit incremented to "2." For example, the embodiment depicted in FIG. 10 includes a catheter assembly 220 that may, in some respects, resemble the catheter assembly 120 of FIG. 1. Relevant disclosure set forth above regarding similarly identified features thus may not be repeated hereafter. Moreover, specific features of the catheter assembly 120 and related components shown in FIGS. 1-2B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the vascular access device 200 and related components depicted in FIG. 10. Any suitable combination of the features, and variations of the same, described with respect to the vascular access device 100 and related components illustrated in FIGS. 1-9B can be employed with the vascular access device 200 and related components of FIG. 10, and vice versa. This pattern of disclosure applies equally to further embodiments depicted in subsequent figures and described hereafter, wherein the leading digits may be further incremented.

FIG. 10 depicts another embodiment of a vascular access device 200. FIG. 10 illustrates a portion of the vascular access device 200 that includes a catheter assembly 220. The catheter assembly 220 includes a strain relief member 225 coupled to a distal hub 230. A needle 251 extends through the strain relief member 225 and the distal hub 230. The needle 251 includes a proximal port 255 that is in fluid communication with a needle lumen 253. An annular space 290' is disposed between an outer surface of the needle 251 and an inner surface of a catheter body 221. The strain relief member 225 includes a circumferential radial inwardly extending rib or ring 293 that is disposed proximal to the proximal port 255. The rib 293 may be configured to apply a circumferential force to the catheter body 221. The circumferential force may collapse the catheter body against the needle 251 to restrict the annular space 290' proximal to the proximal port 255. When the annular space 290' is restricted by the rib 293, flashback blood may be restricted from flowing proximally of the rib 293 and into the distal hub 230 such that the flashback blood is directed into the needle lumen 253 through the proximal port 255.

In some embodiments, the needle 251 may include a circumferential radial outwardly extending bump disposed proximal to the proximal port 255. The bump may be configured to restrict the annular space 290' and restrict flashback blood from flowing into the distal hub 230 such that the flashback blood is directed into the needle lumen 253 through the proximal port 255. In other embodiments, a proximal portion of the needle 251 proximal of the proximal port 255 may have a larger diameter than a distal portion of the needle 251 distal of the proximal port 255. The larger diameter portion may be configured to restrict the annular space 290' and restrict flashback blood from flowing into the distal hub 230 such that the flashback blood is directed into the needle lumen 253 through the proximal port 255.

Figure 11:
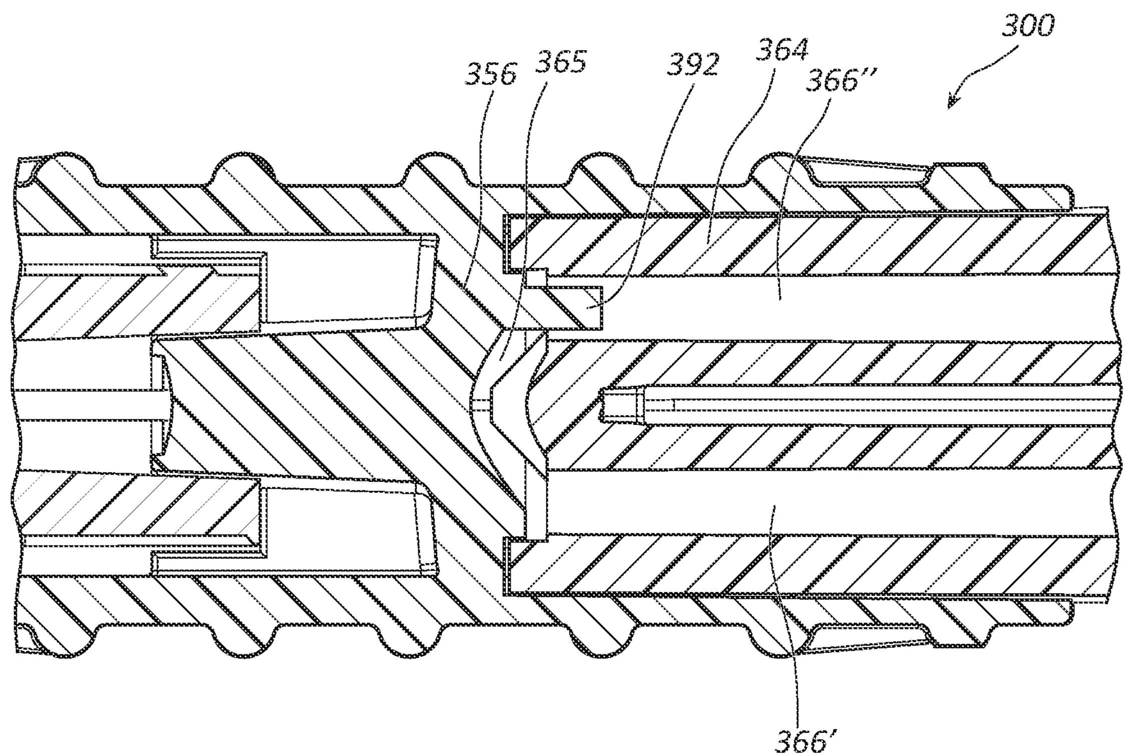
FIG. 11 is a cross-sectional view of a portion of another vascular access device.

FIG. 11 depicts another embodiment of a vascular access device 300. FIG. 11 illustrates a portion of the vascular access device 300 that includes a needle hub 356 and a barrel 364. A distal end of the barrel 364 is coupled to a proximal end of the needle hub 356. A return chamber 365 is disposed between the needle hub 356 and the barrel 364. The return chamber 365 is in fluid communication with flashback channels 366', 366" longitudinally disposed within the barrel 364. A flow restrictor 392 may extend proximally from the needle hub 356 into a distal portion of the flashback channel 366". An outer diameter of the flow restrictor 392 may be smaller than an inner diameter of the distal portion the flashback channel 366". In some embodiments, the flow restrictor 392 comprises a protrusion extending proximally from the needle hub 356 into the flashback channel 366". An outer diameter of the protrusion is less than an inner diameter of the flashback channel 366".

The flow restrictor 392 may be configured to restrict flashback blood from flowing into the flashback channel 366". When the flow restrictor 392 is disposed within the flashback channel 366", flashback blood may initially flow from the return chamber 365 into the flashback channel 366' because the flashback channel 366' is unrestricted at its distal end. After the flashback channel 366' is filled with flashback blood, the flashback blood may then flow from the return chamber 365 into the flashback channel 366". This technique may produce a faster blood level rate to facilitate proper placement of the vascular access device 300 in a blood vessel.

In other embodiments, the inner diameter of the distal portion of the flashback channel 366" may be smaller than an inner diameter of the flashback channel 366' such that the flashback channel 336' may fill with flashback blood prior to the filling of the flashback channel 366" with flashback blood.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term “substantially.” For each such reference, it is to be understood that, in some embodiments, the value, feature, or characteristic may be specified without approximation. For example, where qualifiers such as “about” and “substantially” are used, these terms include within their scope the qualified words in the absence of their qualifiers. For example, where the term “substantially perpendicular” is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A vascular access device, comprising:

a needle assembly, comprising:

a needle hub;

a needle coupled to the needle hub, the needle comprising:

a distal end;

a needle lumen extending from the distal end of the needle;

a distal port extending from an outside surface of the needle to the needle lumen; and a proximal port extending from the outside surface of the needle to the needle lumen;

a catheter assembly disposed over a portion of the needle assembly, the catheter assembly comprising:

a catheter hub;

an elongate tube coupled to the catheter hub; and a barrel assembly coupled to the needle hub, the barrel assembly comprising:

an elongate barrel comprising a first flashback channel and a second flashback channel;

a slider member slidably coupled to the elongate barrel; and a guidewire coupled to the slider member, wherein the guidewire is configured to be slidably disposed within the needle lumen; and a flow restrictor operably coupled to the first flashback channel, wherein the second flashback channel is configured to fill with flashback blood prior to the first flashback channel filling with the flashback blood, the flow restrictor comprising a protrusion extending proximally from the needle hub into the first flashback channel, and wherein an outer diameter of the protrusion is less than an inner diameter of the first flashback channel, wherein the guidewire comprises a proximal portion and a linearly shaped distal portion, wherein a diameter of the linearly shaped distal portion of the guidewire is greater than a diameter of the proximal portion of the guidewire, and wherein the linearly shaped distal portion of the guidewire is configured to inhibit blood flow within the needle lumen around the linearly shaped distal portion of the guidewire between the distal port and the proximal port when the linearly shaped distal portion of the guidewire is disposed between the distal port and the proximal port.

2. The vascular access device of claim 1, wherein the needle hub further comprises laterally extending wing grips.

3. The vascular access device of claim 1, further comprising a strain relief member comprising a circumferential radial inwardly directed rib configured to apply a radial inwardly directed force to the elongate tube.

4. The vascular access device of claim 1, wherein the needle hub further comprises a return chamber in fluid communication with the lumen of the needle and at least one flashback channel of the first flashback channel or the second flashback channel.

5. The vascular access device of claim 1, wherein the linearly shaped distal portion of the guidewire comprises a proximal end and a distal end, and wherein the distal end of the linearly shaped distal portion of the guidewire is disposed proximal to the distal port of the needle and the proximal end of the linearly shaped distal portion of the guidewire is disposed distal to the proximal port of the needle.

6. The vascular access device of claim 1, further comprising a coil that is disposed around the linearly shaped distal portion of the guidewire, wherein a diameter of the coil is slightly smaller than a diameter of the needle lumen.

7. The vascular access device of claim 1, further comprising a coil that is disposed around the linearly shaped distal portion of the guidewire, wherein the coil has a length such that the coil extends from adjacent the distal port to adjacent the proximal port, thereby substantially occluding the needle lumen between the distal port and the proximal port.

8. A method of placing a vascular access device into a blood vessel, comprising:

obtaining the vascular access device comprising a needle assembly, a catheter assembly, and a barrel assembly coupled to a needle hub of the needle assembly;

puncturing the blood vessel with a needle of the needle assembly of the vascular access device;

inducing a blood flow through a distal portion of a lumen of the needle;

directing the blood flow from the distal portion of the lumen of the needle through a needle distal port into an elongate annular space defined by an inner surface of a catheter body of the catheter assembly and an outer surface of the needle;

directing the blood flow from the elongate annular space through a needle proximal port into the needle lumen, and filling a first flashback channel of an elongate barrel of the barrel assembly with flashback blood prior to filling a second flashback channel with the flashback blood responsive to a flow restrictor operably coupled to the second flashback channel, the flow restrictor comprising a protrusion extending proximally from the needle hub into the second flashback channel, and wherein an outer diameter of the protrusion is less than an inner diameter of the second flashback channel, wherein directing the blood flow comprises inhibiting the needle lumen with a guidewire between the needle distal port and the needle proximal port, wherein the guidewire comprises a proximal portion and a distal portion, the distal portion of the guidewire comprising an elongated shape and extending from proximate the needle distal port to proximate the needle proximal port, and wherein a diameter of the distal portion of the guidewire is greater than a diameter of the proximal portion of the guidewire.

9. The method of claim 8, further comprising visually observing blood flowing through the elongate annular space.

10. The method of claim 8, further comprising:

visually observing blood flowing from the needle lumen into a return chamber; and visually observing blood flowing from the return chamber into at least one flashback channel of the first flashback channel and the second flashback channel.

11. The method of claim 10, further comprising visually observing blood flowing into the first flashback channel prior to visually observing blood flowing into the second flashback channel.

12. A vascular access device, comprising:

a needle assembly, comprising:

a needle hub;

a needle coupled to the needle hub, the needle comprising a distal end, a needle lumen extending from the distal end of the needle, a distal port extending from an outside surface of the needle to the needle lumen, and a proximal port extending from the outside surface of the needle to the needle lumen;

a catheter assembly disposed over a portion of the needle assembly, the catheter assembly comprising a catheter hub and an elongate tube coupled to the catheter hub; and a barrel assembly coupled to the needle hub, the barrel assembly comprising:

an elongate barrel comprising a first flashback channel and a second flashback channel;

a slider member slidably coupled to the elongate barrel; and a guidewire coupled to the slider member, wherein the guidewire is configured to be slidably disposed within the needle lumen; and a flow restrictor operably coupled to the first flashback channel, wherein the second flashback channel is configured to fill with flashback blood prior to the first flashback channel filling with the flashback blood, the flow restrictor comprising a protrusion extending proximally from the needle hub into the first flashback channel, and wherein an outer diameter of the protrusion is less than an inner diameter of the first flashback channel.

13. The vascular access device of claim 12, wherein the guidewire comprises a proximal portion and a distal portion having a diameter greater than a diameter of the proximal portion of the guidewire.

14. The vascular access device of claim 13, wherein:

the distal portion of the guidewire comprises a proximal end and a distal end; and wherein the distal end of the distal portion of the guidewire is disposed proximal to the distal port of the needle and the proximal end of the distal portion of the guidewire is disposed distal to the proximal port of the needle.

15. The vascular access device of claim 12, wherein the guidewire comprises a distal portion configured to inhibit blood flow within the needle lumen around the distal portion of the guidewire between the distal port and the proximal port when the distal portion of the guidewire is disposed between the distal port and the proximal port.

16. The vascular access device of claim 12, wherein the needle hub further comprises laterally extending wing grips.

17. The vascular access device of claim 12, further comprising a strain relief member comprising a circumferential radial inwardly directed rib configured to apply a radial inwardly directed force to the elongate tube.

18. The vascular access device of claim 12, wherein the needle hub further comprises a return chamber in fluid communication with the lumen of the needle and at least one flashback channel of the first flashback channel or the second flashback channel.

* * * * *